US012377221B2

(12) United States Patent
Maxfield

(10) Patent No.: US 12,377,221 B2
(45) Date of Patent: Aug. 5, 2025

(54) TRIGGERING MECHANISM FOR A MEDICAMENT DELIVERY DEVICE

(71) Applicant: SHL MEDICAL AG, Zug (CH)

(72) Inventor: Brian Maxfield, Delray Beach, FL (US)

(73) Assignee: SHL Medical AG, Zug (CH)

( * ) Notice: Subject to any disclaimer, the term of this patent is extended or adjusted under 35 U.S.C. 154(b) by 937 days.

(21) Appl. No.: 17/610,813

(22) PCT Filed: Apr. 27, 2020

(86) PCT No.: PCT/EP2020/061608
§ 371 (c)(1),
(2) Date: Nov. 12, 2021

(87) PCT Pub. No.: WO2020/233946
PCT Pub. Date: Nov. 26, 2020

(65) Prior Publication Data
US 2022/0203034 A1     Jun. 30, 2022

Related U.S. Application Data

(60) Provisional application No. 62/849,275, filed on May 17, 2019.

(30) Foreign Application Priority Data

May 27, 2019  (EP) ..................................... 19176654

(51) Int. Cl.
*A61M 5/24*  (2006.01)
*A61M 5/32*  (2006.01)
*A61M 5/20*  (2006.01)

(52) U.S. Cl.
CPC ........ *A61M 5/2466* (2013.01); *A61M 5/3202* (2013.01); *A61M 5/3243* (2013.01);
(Continued)

(58) Field of Classification Search
CPC .............. A61M 5/2466; A61M 5/3202; A61M 5/3243; A61M 5/3293; A61M 2005/2013; A61M 2005/2474; A61M 2005/3267
See application file for complete search history.

(56) References Cited

U.S. PATENT DOCUMENTS

2013/0035644 A1*  2/2013  Giambattista ....... A61M 5/2466
                                                                   604/192
2017/0080165 A1*  3/2017  Soerensen ........... A61M 5/3202
2018/0339105 A1*  11/2018  Schader .............. A61M 5/3204

FOREIGN PATENT DOCUMENTS

WO    2011/126439 A1    10/2011
WO    2015/140262 A1    9/2015
(Continued)

OTHER PUBLICATIONS

International Search Report and Written Opinion for Int. App. No. PCT/EP2020/061608, mailed Jun. 3, 2020.

*Primary Examiner* — Michael J Tsai
*Assistant Examiner* — Justin L Zamory
(74) *Attorney, Agent, or Firm* — McDonnell Boehnen Hulbert & Berghoff LLP

(57) ABSTRACT

A triggering mechanism for a medicament delivery device, wherein the triggering mechanism comprises: a delivery member cover, a rotator, and a delivery member hub, wherein the delivery member cover is configured to move linearly relative to the rotator, wherein the delivery member cover is configured to cause rotation of the rotator when the delivery member cover is moved linearly in a first direction, and wherein the rotator is configured to cause linear movement of the delivery member hub in a second direction opposite to the first direction when the rotator is rotated.

17 Claims, 4 Drawing Sheets

(52) U.S. Cl.
CPC ... *A61M 5/3293* (2013.01); *A61M 2005/2013* (2013.01); *A61M 2005/2474* (2013.01); *A61M 2005/3267* (2013.01)

(56) References Cited

FOREIGN PATENT DOCUMENTS

| | | |
|---|---|---|
| WO | 2017/089278 A1 | 6/2017 |
| WO | 2017/089287 A1 | 6/2017 |
| WO | 2018/136840 A1 | 7/2018 |

* cited by examiner

TRIGGERING MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2020/061608 filed Apr. 27, 2020, which claims priority to U.S. Provisional Application No. 62/849,275, filed May 17, 2019, and European Patent Application No. 19176654.2 filed May 27, 2019. The entire disclosure contents of these applications are herewith incorporated by reference into the present application.

TECHNICAL FIELD

The present disclosure generally relates to medicament delivery devices.

BACKGROUND

WO2018/136840 discloses an auto-injector which includes a first subassembly having a cartridge holder configured to receive a medication cartridge, a hollow injection needle having a longitudinal cavity, and a movable needle shield. The auto-injector includes a second subassembly which includes a housing and a movable plunger rod. The first subassembly comprises a needle holder for retaining the needle. The needle holder is movable between a first position and a second position. In the first position the needle cavity is not in fluid communication with an interior of the medication cartridge. In the second position, the needle cavity is in fluid communication with the interior of the medication cartridge. The auto-injector also has a cap, releasably attached to the first subassembly. When the cap is removed from the subassembly, the needle moves from the first position to the second position to cause a distal end of the needle to pierce a septum of the cartridge. In particular, rotation of the cap causes distal movement of the needle holder and needle towards the second position.

Some users may have functional disabilities such as rheumatism, which may cause difficulties to interact with the auto-injector disclosed in WO2018/136840. It may in particular be difficult for a user to unscrew the cap.

SUMMARY

An object of the present disclosure is to provide a triggering mechanism for a medicament delivery device which solves or at least mitigates problems of the prior art.

There is hence, according to a first aspect of the present disclosure provided, a triggering mechanism for a medicament delivery device, wherein the triggering mechanism comprises: a delivery member cover, a rotator, and a delivery member hub, wherein the delivery member cover is configured to move linearly relative to the rotator, wherein the delivery member cover is configured to cause rotation of the rotator when the delivery member cover is moved linearly in a first direction, and wherein the rotator is configured to cause linear movement of the delivery member hub in a second direction opposite to the first direction when the rotator is rotated.

The first direction may be a proximal direction. The second direction may be a distal direction. The proximal direction is defined along a central axis of the triggering mechanism, from a rear end of the triggering mechanism towards a front end of the triggering mechanism. The distal direction is opposite to the proximal direction.

The triggering mechanism provides a dual cam-type configuration, in the sense that linear movement of the delivery member cover in the first direction causes rotation of the rotator, which in turn causes linear movement of the delivery member hub in a second direction opposite to the first direction. The delivery member hub may thereby be moved towards a medicament container by linear motion of the delivery member cover, without necessarily having to apply any rotational motion to any component of the triggering mechanism, or a medicament delivery device fitted with the triggering mechanism.

According to one embodiment the delivery member cover is configured to receive the rotator and the rotator is configured to receive the delivery member hub. The delivery member cover, the rotator and the delivery member hub may hence be arranged concentrically.

One embodiment comprises a double-sided needle fixedly arranged in the delivery member hub. The double-sided needle may have a proximal end portion and a distal end portion. The proximal end portion extends in the proximal direction from the delivery member hub and the distal end portion extends in the distal direction from the delivery member hub.

According to one embodiment the delivery member cover is provided with a radially inward extending protrusion configured to interact with the rotator.

According to one embodiment the rotator has an external surface provided with an outer guide structure configured to interact with the radially inwards extending protrusion, enabling transformation of linear motion of the delivery member cover to rotational motion of the rotator.

According to one embodiment the outer guide structure comprises a first helical rib arranged in a first helical direction, configured to interact with the radially inwards extending protrusion.

According to one embodiment the delivery member hub has a radially outwards extending hub protrusion configured to interact with the rotator.

According to one embodiment the rotator has an inner surface provided with an inner guide structure configured to interact with the radially outwards extending hub protrusion, enabling transformation of rotating motion of the rotator to linear motion of the delivery member hub.

According to one embodiment the inner guide structure comprises a second helical rib arranged in a second helical direction opposite to the first helical direction, configured to interact with the radially outwards extending hub protrusion.

One embodiment comprises a medicament container holder configured to receive the delivery member hub, wherein the medicament container holder is provided with a slit through which the radially outwards extending hub protrusion extends, the slit being configured to prevent rotation of the delivery member hub relative to the rotator.

According to one embodiment the slit is provided in a proximal end portion of the medicament container holder, and wherein the rotator is configured to receive the proximal end portion.

The medicament container holder is configured to hold a medicament container. The medicament container may be provided with a septum. The distal end portion of the double-edged needle may be configured to pierce the septum as the delivery member hub is moved in the second direction.

According to one embodiment the delivery member cover is configured to be rotationally locked relative to the rotator.

One embodiment comprises a cap configured to be mounted around a proximal end portion of the delivery member cover, the cap being configured to hold the delivery member cover in an initial position in which the delivery member cover is biased in the first direction, wherein removal of the cap causes the delivery member cover to move linearly in the first direction.

The cap may for example directly abut the delivery member cover to hold the delivery member cover in the initial position. For example, the cap may have an internal structure which bears against the proximal end face of the delivery member cover to thereby hold the delivery member cover in the initial position.

According to one example, a housing of the medicament delivery device may have flexible arms arranged to engage with the delivery member cover. When the cap is mounted to the housing, the cap may be configured to hold the arms such they engage with the delivery member cover and hold the delivery member cover in the initial position. When the cap is removed, the arms may be able to flex such that they are released from engagement with the delivery member cover.

The cap may hence be configured to directly or indirectly hold the delivery member cover in the initial position when mounted to the housing.

One embodiment comprises a knob configured to hold the delivery member cover in the initial position in which the delivery member cover is biased in the first direction, wherein actuation of the knob causes the delivery member cover to move linearly in the first direction.

There is according to a second aspect of the present disclosure provided a medicament delivery device comprising: the housing, and a triggering mechanism according to the first aspect, wherein the delivery member cover is rotationally locked relative to the housing.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
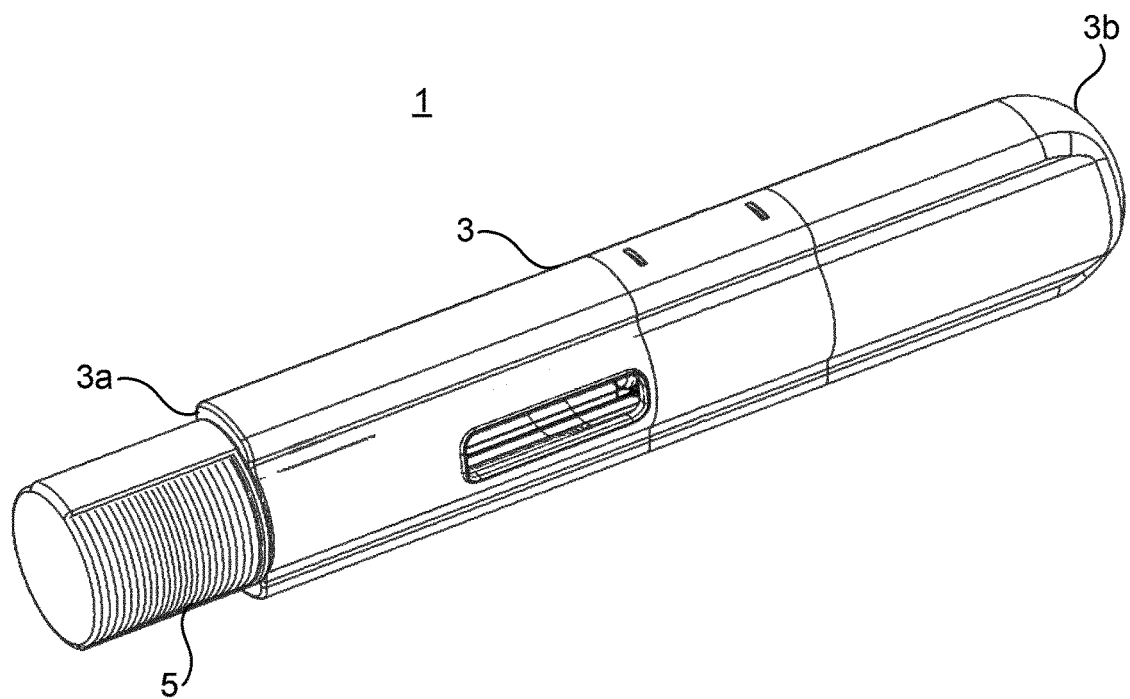
FIG. 1 is a perspective view of an example of a medicament delivery device.

FIG. 1 shows a perspective view of an example of a medicament delivery device 1. The medicament delivery device 1 may for example be an auto-injector.

The exemplified medicament delivery device 1 comprises a housing 3. The housing 3 has a proximal end 3a and a distal end 3b. According to the present example, the distal end 3b also forms the distal end, or rear end, of the medicament delivery device 1. Other configurations are however also envisaged as alternatives. For example, the medicament delivery device could alternatively be provided with an actuator such as a knob, forming a distal end of the medicament delivery device.

The exemplified medicament delivery device 1 comprises a cap 5. The cap 5 forms a proximal end of the medicament delivery device 1 in the initial state of the medicament delivery device 1 shown in FIG. 1. The initial state of the medicament delivery device 1 is a state prior to a primed state and subsequent activation of the medicament delivery device 1.

The cap 5 is configured to be attached to the housing 3 of the medicament deliver device 1. Alternatively, or additionally, the cap 5 may be attached to one or more internal components of the medicament delivery device 1, not visible in FIG. 1. The cap 5 is configured to be removed from its attachment to the housing 3. The medicament delivery device 1 will thereby attain its primed state, as will be described in more detail in what follows.

Figure 2:
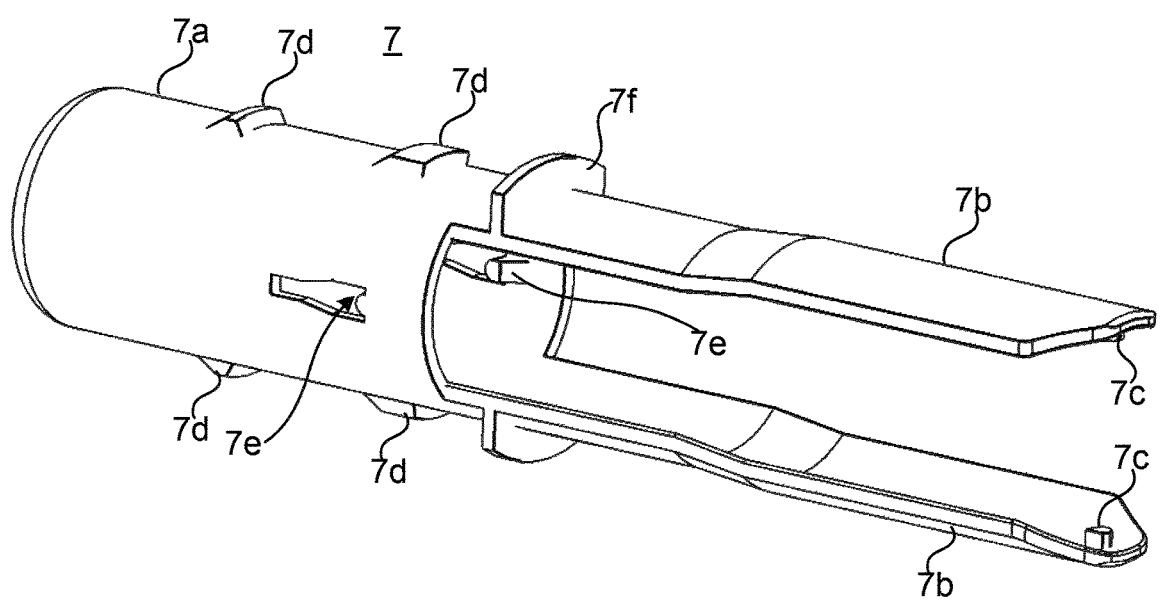
FIG. 2 is a perspective view of a delivery member cover.

The medicament delivery device 1 comprises a delivery member cover, not shown in FIG. 1. FIG. 2 shows a perspective view of an example of a delivery member cover 7. The delivery member cover 7 is configured to be arranged in the housing 3. The delivery member cover 7 is configured to be movably arranged in the housing 3. The delivery member cover 7 is configured to be moved linearly relative to the housing 3. The delivery member cover 7 is arranged rotationally locked relative to the housing 3. The delivery member cover 7 is configured to be biased in the proximal direction. The delivery member cover 7 is configured to be arranged fixed in an initial position in the initial state of the medicament delivery device 1. In the initial position, the cap 5 holds the delivery member cover 7 in the initial position. By removing the cap 5, the delivery member cover 7 is moved in a first direction, in the following the proximal direction relative to the housing 3. The delivery member cover 7 is in particular moved in the proximal direction towards an extended position relative to the housing 3. The procedure of removing the cap 5, whereby the delivery member cover 7 is moved to the extended position may be referred to as priming. By performing this procedure, the medicament delivery member 1 attains its primed state.

The delivery member cover 7 has a generally tubular proximal end portion 7a. The delivery member cover 7 comprises two legs 7b extending distally from the proximal end portion 7a. The delivery member cover 7 is an elongated structure. The legs 7b are provided with two radially inwards extending structures 7c. According to the present example, the radially inwards structures 7c engage with a power pack assembly of the medicament delivery device 1. The radially inwards extending structures 7c may provide rotational locking of the delivery member cover 7 relative to the housing 3 when the delivery member cover 7 is in the extended position.

The radially inwards extending structures 7c may also be configured to interact with the power pack assembly when the delivery member cover 7 is moved in the distal direction from the extended position to thereby activate the medicament delivery device 1. This operation is however not the subject of the present application, and since this interaction may be performed according to any useful method, it will not be described any further herein.

The delivery member cover 7 may further comprise one or more radially outwards extending structures 7d. The radially outwards extending structures 7d may be provided on an external surface of the tubular proximal end portion 7a of the delivery member cover 7. The radially outwards extending structures 7d may be configured to engage with an internal structure, such as corresponding longitudinal channels in the housing 3 to prevent rotation of the delivery member cover 7. The radially outwards extending structures 7d may for example be configured to prevent rotation of the delivery member cover 7 relative to the housing 3 when the delivery member cover 7 has been pushed a certain distance in the distal direction from the extended position.

The exemplified delivery member cover 7 has one or more radially inward extending protrusions 7e.

The exemplified delivery member cover 7 cover is also provided with flange structures 7f. The medicament delivery device 1 may include a resilient member, such as a spring, arranged around the delivery member cover 7 bearing against distal surfaces of the flange structures 7f to bias the delivery member cover 7 in the proximal direction.

Figure 3:
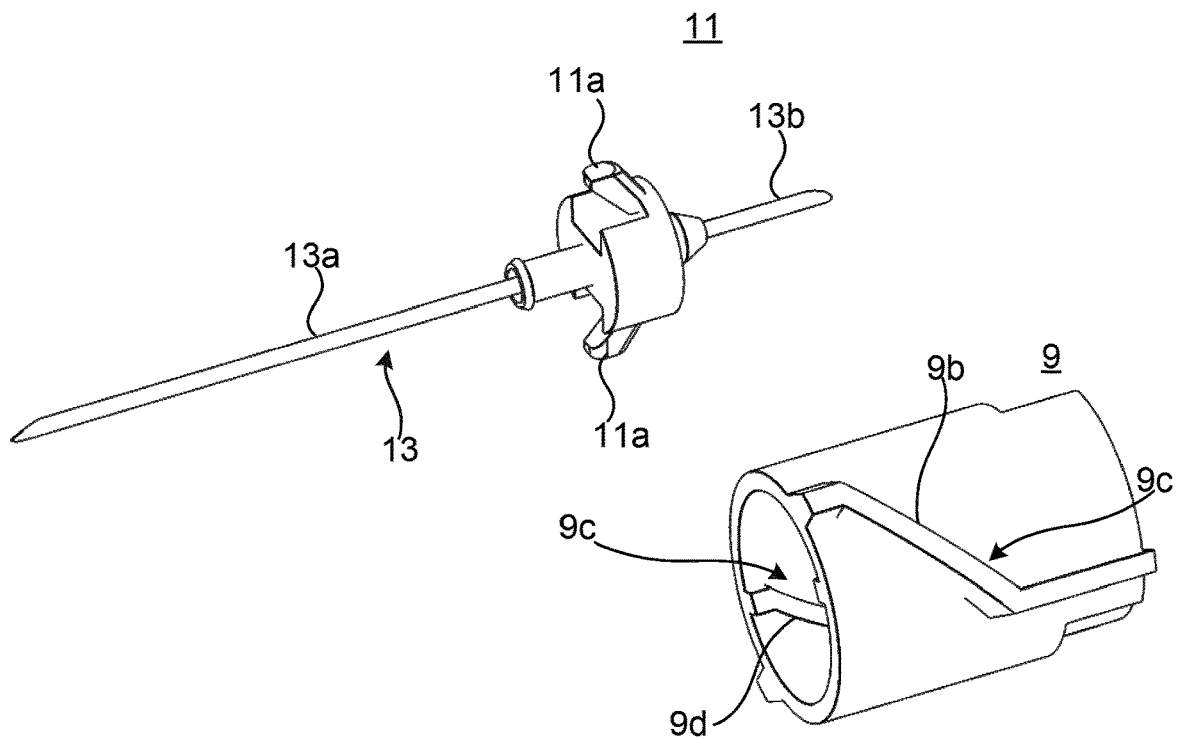
FIG. 3 depicts a perspective view of a delivery member hub and a rotator.

Turning now to FIG. 3, the medicament delivery device 1 furthermore comprises a rotator 9 and a delivery member hub 11. The delivery member cover 7, the rotator 9 and the delivery member hub 11 form or form part of a triggering mechanism 10, shown in FIG. 6.

The rotator 9 is configured to be arranged in the delivery member cover 7. The delivery member hub 11 is configured to be arranged in the rotator 9. The delivery member cover 7, the rotator 9, and the delivery member hub 11 are hence arranged concentrically.

The medicament delivery device 1 also comprises a double-edged needle 13. The double-edged needle 13 is fixedly arranged in and extends through the delivery member hub 11. The double-edged needle 13 has a proximal end portion 13a extending proximally from the delivery member hub 11 and a distal end portion 13b extending distally from the delivery member hub 11. The delivery member hub 13 has radially outwards extending hub protrusions 11a. In the example shown in FIG. 3, the radially outwards extending hub protrusions 11a extend in opposite radial directions.

The rotator 9 has an external surface provided with an outer guide structure 9a. The outer guide structure 9a comprises first helical ribs 9b, of which one is shown in FIG. 3. The first helical ribs 9b are arranged in a first helical direction along the external surface of the rotator 9.

Figure 4:
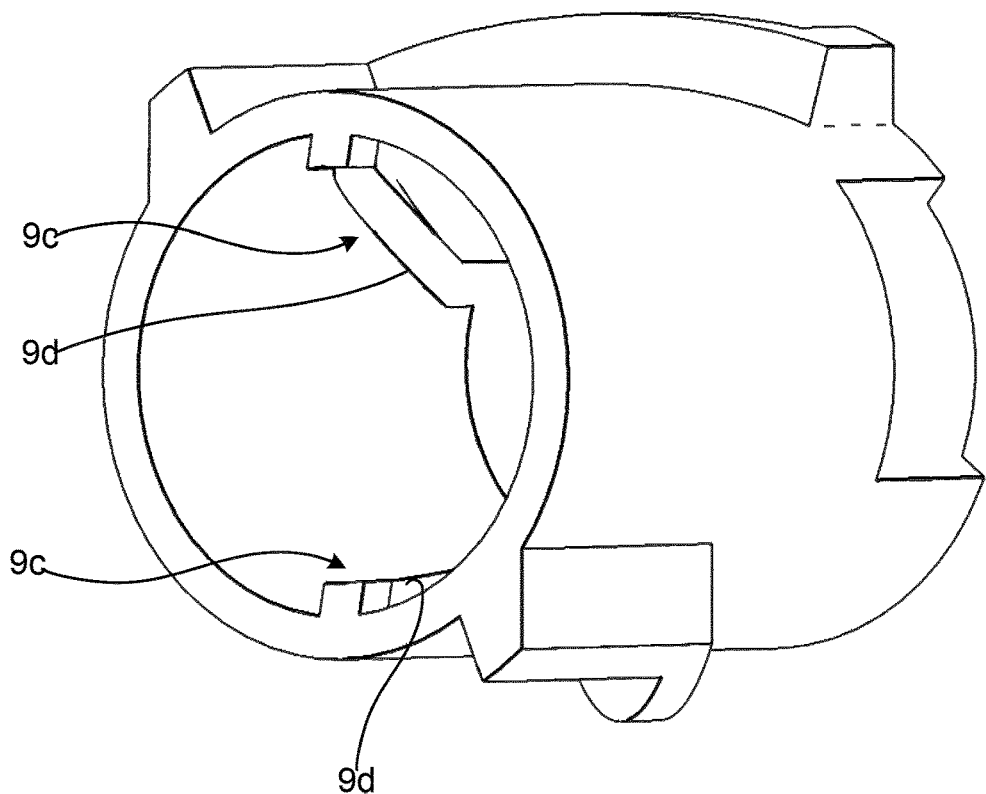
FIG. 4 is a perspective view of the rotator.

The rotator 9 has an inner surface provided with an inner guide structure 9c. The inner guide structure 9c comprises second helical ribs 9d. The second helical ribs 9d are arranged in a second helical direction along the inner surface of the rotator 9. The second helical direction is opposite to the first helical direction. This configuration can better be seen in FIG. 4.

The delivery member cover 7 is configured to interact with the rotator 9. The radially inwards extending protrusions 7e of the delivery member cover 7 are configured to interact with a respective first helical rib 9b of the rotator 9. Thus, linear movement of the delivery member cover 7 from the initial position in the proximal direction is transformed and causes rotation of the rotator 9 when the delivery member cover 7 has moved a predetermined distance in the proximal direction.

The rotator 9 is configured to interact with the delivery member hub 11. The radially outwards extending hub protrusions 11a of the delivery member hub 11 are configured to interact with the second helical ribs 9d. The delivery member hub 11 is configured to be rotationally locked relative to the rotator 9. Hereto, rotation of the rotator 9 is transformed and causes linear movement of the delivery member hub 11 relative to the rotator 9. This linear movement of the delivery member hub 11 is a second direction in the following the distal direction, opposite to the first direction, because of the second helical direction of the second helical ribs 9d. The double-edged needle 13 is hence also moved in the distal direction the same distance as the delivery member hub 11.

Figure 5:
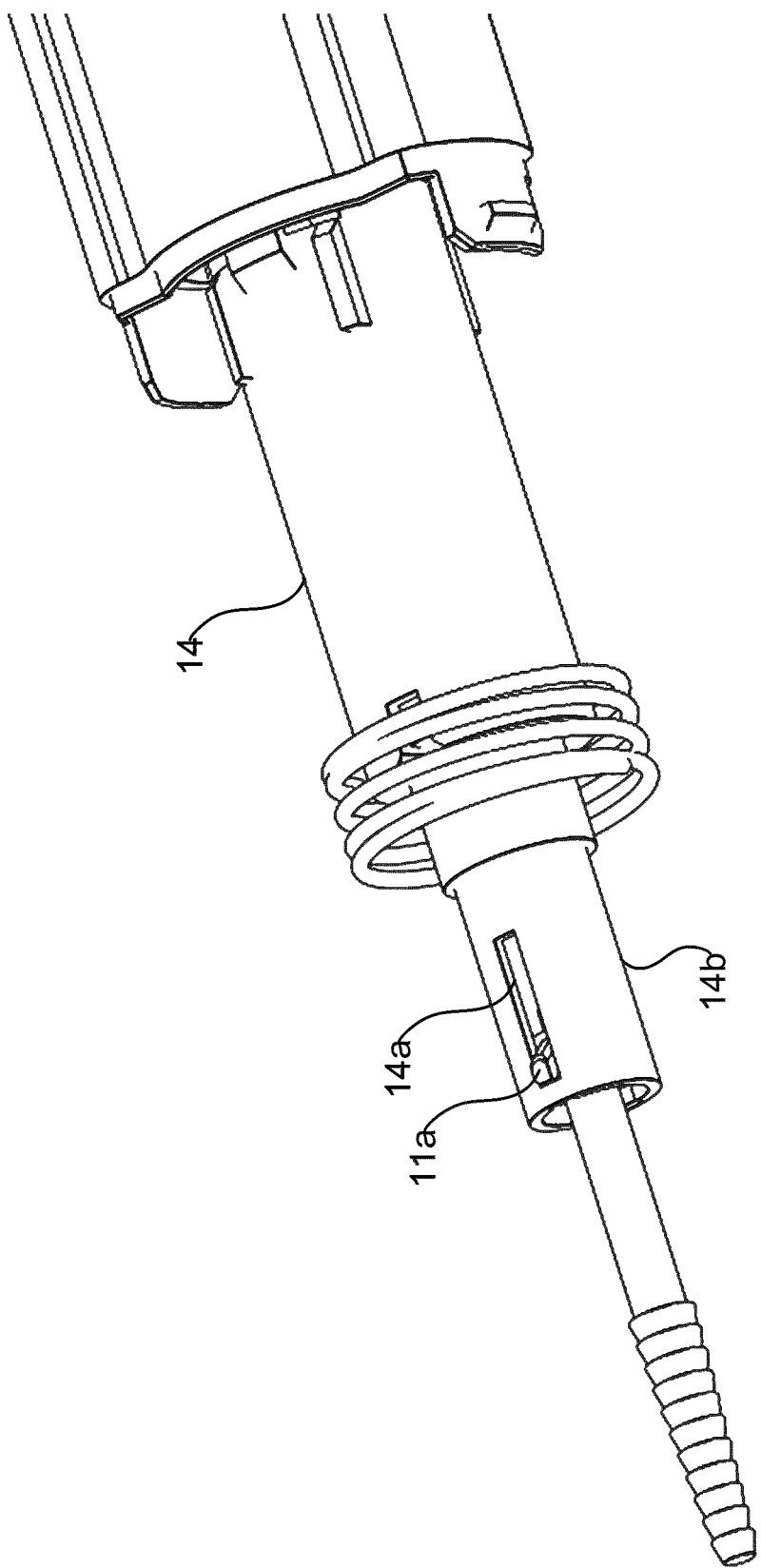
FIG. 5 shows a perspective view of the medicament delivery device in FIG. 1, with components removed to expose certain internal components.

Turning now to FIG. 5, the medicament delivery device 1 comprises a medicament container holder 14. The medicament container holder 14 is configured to hold a medicament container. The medicament container holder 14 is configured to be arranged in the housing 3. The medicament container holder 14 has slits 14a configured to receive a respective one of the radially outwards extending hub protrusions 11a. The medicament container holder 14 may have a proximal end portion 14b, and the slits 14a may be provided in the proximal end portion 14b. The rotator 9 is configured to receive the proximal end portion 14b. The slits 14a are configured to prevent rotation of the delivery member hub 11 by interacting with the radially outwards extending hub protrusions 11a. The slits 14a are designed to allow the delivery member hub 11 to move in the distal direction from an initial delivery member hub position shown in FIG. 5. The radially outwards extending hub protrusions 11a are hence allowed to move in the slits 14a distally towards a respective distal end of the slits 14a.

Figure 6:
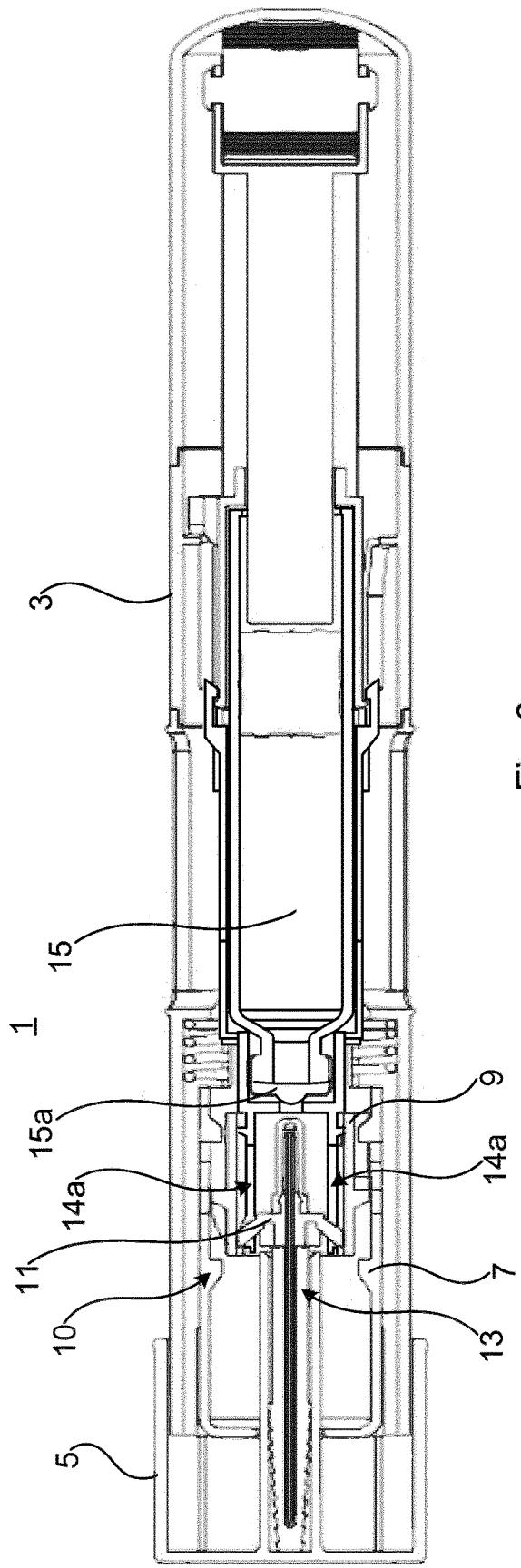
FIG. 6 shows a longitudinal section of the medicament delivery device in FIG. 1 in the initial state also depicted in FIG. 1.
Figure 7:
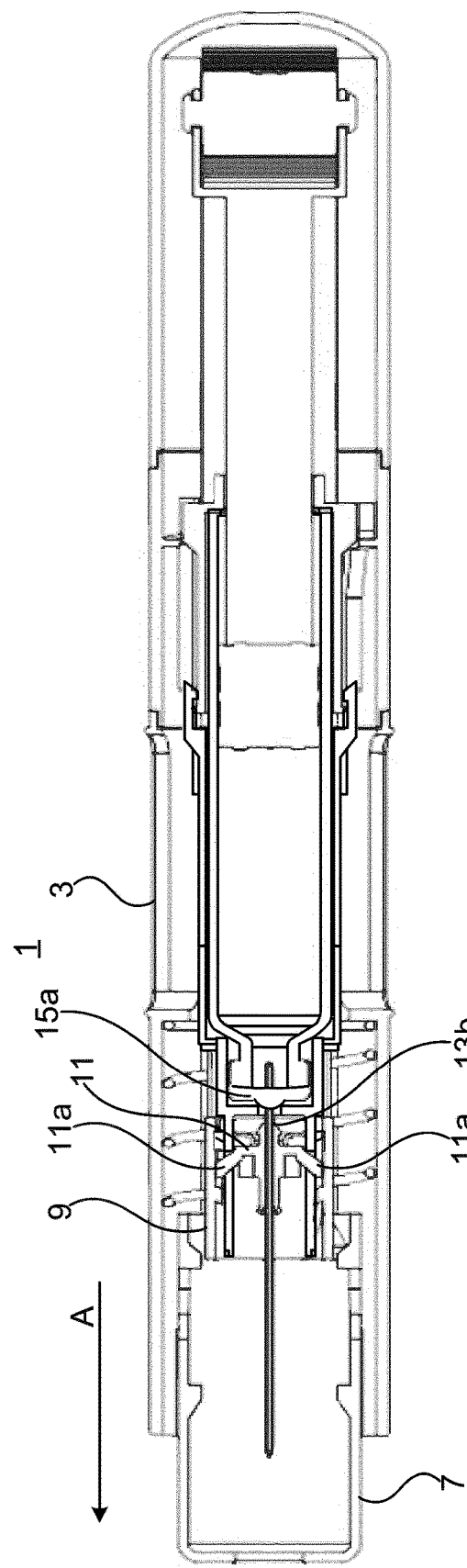
FIG. 7 is a longitudinal section of the medicament delivery device in FIG. 1 in a primed state.

The operation of the medicament delivery device 1 will now be described with reference to FIGS. 6 and 7. FIGS. 6 and 7 demonstrate how the medicament delivery device 1 attains the primed state from the initial state.

In FIG. 6, the medicament delivery device 1 is in the initial state. The cap 5 is attached to the housing 3. The delivery member cover 7 is thereby arranged in the initial position, in which it extends from the housing 3 and into the cap 5. The delivery member hub 11 is arranged in the initial delivery member hub position. The radially outwards extending hub protrusions 11a are hence arranged proximally in the slits 14a.

The medicament delivery device 1 comprises a medicament container 15 arranged in the housing 3. The medicament container 15 has a septum 15a. The septum 15a is arranged distally relative to the double-edged needle 13 and aligned with the double-edged needle 13. In the initial state of the medicament delivery device 1, the septum 15a seals the medicament container 15.

In FIG. 7 the medicament delivery device 1 is in the primed state. The primed state is attained from the initial state by removing the cap 5. The proximally biased delivery member cover 7 is thereby moved in the proximal direction as shown by arrow A. As a result, the rotator 9 is rotated and the delivery member hub 11 is moved in the distal direction. The radially outwards extending hub protrusions 11a are hence moved in the distal direction in the slits 14a, whereby the distal end portion 13b of the double-edged needle 13 pierces the septum 15a.

In the primed state, the medicament delivery device 1 is ready to be activated. Medicament delivery may hence be commenced. Activation is achieved by pushing the delivery member cover 7 into the housing 3.

Instead of holding the delivery member cover 7 in the initial position with the cap 5, the delivery member cover 7 could alternatively be held in the initial position by an actuator mechanism comprising a knob, as is known to the skilled person. By actuating the knob, the delivery member cover would be released and move in the proximal position. The medicament delivery device would hence attain its primed state.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A triggering mechanism for a medicament delivery device, wherein
the triggering mechanism comprises:
a delivery member cover,
a rotator, and
a delivery member hub,
wherein the delivery member cover is configured to move linearly relative to the rotator,
wherein the delivery member cover is configured to cause rotation of the rotator when the delivery member cover is moved linearly in a first direction,
wherein the rotator is configured to cause linear movement of the delivery member hub in a second direction opposite to the first direction when the rotator is rotated,
wherein the delivery member hub has a radially outwards extending hub protrusion configured to interact with the rotator, and
wherein the rotator has an inner surface provided with an inner guide structure configured to interact with the radially outwards extending hub protrusion, enabling transformation of rotating motion of the rotator to linear motion of the delivery member hub.

2. The triggering mechanism as claimed in claim 1, wherein the delivery member cover is configured to receive the rotator and the rotator is configured to receive the delivery member hub.

3. The triggering mechanism as claimed in claim 1, comprising a double-sided needle fixedly arranged in the delivery member hub.

4. The triggering mechanism as claimed in claim 1, wherein the delivery member cover is provided with a radially inward extending protrusion configured to interact with the rotator.

5. The triggering mechanism as claimed in claim 4, wherein the rotator has an external surface provided with an outer guide structure configured to interact with the radially inwards extending protrusion, enabling transformation of linear motion of the delivery member cover to rotational motion of the rotator.

6. The triggering mechanism as claimed in claim 5, wherein the outer guide structure comprises first helical rib arranged in a first helical direction, configured to interact with the radially inwards extending protrusion.

7. The triggering mechanism as claimed in claim 1, wherein
the inner guide structure comprises a second helical rib arranged in a second helical direction opposite to the first helical direction, configured to interact with the radially outwards extending hub protrusion.

8. The triggering mechanism as claimed in claim 1, comprising a medicament container holder configured to receive the delivery member hub, wherein the medicament container holder is provided with a slit through which the radially outwards extending hub protrusion extends, the slit being configured to prevent rotation of the delivery member hub relative to the rotator.

9. The triggering mechanism as claimed in claim 8, wherein the slit is provided in a proximal end portion of the medicament container holder, and wherein the rotator is configured to receive the proximal end portion.

10. The triggering mechanism as claimed in claim 1, wherein the delivery member cover is configured to be rotationally locked relative to the rotator.

11. The triggering mechanism as claimed in claim 1, comprising a cap configured to be mounted around a proximal end portion of the delivery member cover, the cap being configured to hold the delivery member cover in an initial position in which the delivery member cover is biased in the first direction, wherein removal of the cap causes the delivery member cover to move linearly in the first direction.

12. The triggering mechanism as claimed in claim 1, comprising a knob configured to hold the delivery member cover in the initial position in which the delivery member cover is biased in the first direction, wherein actuation of the knob causes the delivery member cover to move linearly in the first direction.

13. A medicament delivery device comprising:
a housing, and
a triggering mechanism as claimed in claim 1, wherein the delivery member cover is rotationally locked relative to the housing.

14. A medicament delivery device comprising:
a housing;
a delivery member cover rotationally fixed relative to the housing and slidably positioned within the housing, where the delivery member cover is biased in a proximal direction;
a rotator operatively engaged with the delivery member cover, where the rotator rotates relative to the delivery member cover when the delivery member cover moves proximally relative to the housing, wherein the rotator has an inner surface provided with an inner guide structure that interacts with the radially outwards extending hub protrusion to transform the rotating motion of the rotator to linear motion of the hub; and
a double ended needle fixedly attached to a hub that is operatively engaged with the rotator such that the rotation of the rotator causes the hub to move distally such that a distal end of the double ended needle will be in fluid communication with a medicament container positioned within the housing.

15. The medicament delivery device of claim 14, wherein the delivery member cover comprises a radially inward extending protrusion that interacts with a guide structure on an external surface of the rotator to cause rotation of the rotator.

16. The medicament delivery device of claim 14 further comprises a medicament container arranged in the housing and comprising a septum arranged distally relative to the double-edged needle and aligned with the double-edged needle; in the initial state of the medicament delivery device, the septum seals the medicament container.

17. The medicament delivery device of claim 14, further comprising a
- cap mounted on a proximal end of the housing,
- wherein removal of the cap from the housing causes the delivery member cover to move in the proximal direction relative to the housing and simultaneously causes the rotation of rotator and distal axial movement of the hub relative to the rotator, and
- wherein the distal axial movement of the hub is caused by engagement of radially outwards extending hub protrusions with an inner surface of the rotator.

* * * * *